(12) United States Patent
Yarden et al.

(10) Patent No.: US 8,714,816 B2
(45) Date of Patent: May 6, 2014

(54) TEMPERATURE SENSOR WITH CALIBRATED ANALOG RESISTIVE OUTPUT

(75) Inventors: Moshe Yarden, Mevasseret Zion (IL); David Sergio Matusevich, Jerusalem (IL)

(73) Assignee: Medisim Ltd., Neve Ilan (IL)

( * ) Notice: Subject to any disclaimer, the term of this patent is extended or adjusted under 35 U.S.C. 154(b) by 770 days.

(21) Appl. No.: 12/880,102

(22) Filed: Sep. 12, 2010

(65) Prior Publication Data

US 2012/0065540 A1 Mar. 15, 2012

(51) Int. Cl.
G01K 7/22 (2006.01)
G01K 7/14 (2006.01)
G01K 15/00 (2006.01)

(52) U.S. Cl.
USPC .......... 374/185; 374/1; 374/100; 702/133

(58) Field of Classification Search
USPC ............ 374/163, 170–173, 183, 185, 100, 1; 600/549, 473, 474; 702/130–136; 340/970.17
See application file for complete search history.

(56) References Cited

U.S. PATENT DOCUMENTS

| | | | |
|---|---|---|---|
| 3,776,040 A * | 12/1973 | Gould, III | 374/185 |
| 3,921,621 A * | 11/1975 | Baessler | 600/549 |
| 4,407,292 A * | 10/1983 | Edrich | 600/430 |
| 4,467,633 A * | 8/1984 | McEwen et al. | 72/203 |
| 5,073,034 A | 12/1991 | Beran et al. | |
| 5,313,185 A * | 5/1994 | DeChurch | 338/22 R |
| 5,655,305 A * | 8/1997 | Fletcher | 374/170 |
| 5,857,777 A * | 1/1999 | Schuh | 374/172 |
| 6,030,342 A | 2/2000 | Amano et al. | |
| 6,086,247 A * | 7/2000 | von Hollen | 374/137 |
| 6,179,786 B1 * | 1/2001 | Young | 600/549 |
| 6,238,354 B1 * | 5/2001 | Alvarez | 600/549 |
| 6,248,083 B1 * | 6/2001 | Smith et al. | 600/585 |
| 6,270,463 B1 * | 8/2001 | Morris et al. | 600/549 |
| 6,292,685 B1 | 9/2001 | Pompei | |
| 6,735,379 B2 * | 5/2004 | Salmon et al. | 392/418 |
| 6,929,611 B2 | 8/2005 | Koch | |
| 7,059,769 B1 * | 6/2006 | Potega | 374/185 |
| 7,625,117 B2 | 12/2009 | Haslett et al. | |
| 7,641,390 B2 | 1/2010 | Shidemantle et al. | |
| 8,328,420 B2 * | 12/2012 | Abreu | 374/208 |
| 2004/0252750 A1 * | 12/2004 | Gruszecki et al. | 374/185 |
| 2005/0245839 A1 | 11/2005 | Stivoric et al. | |
| 2005/0276309 A1 | 12/2005 | Koch | |
| 2006/0122473 A1 * | 6/2006 | Kill et al. | 600/300 |
| 2007/0038048 A1 | 2/2007 | Gerder | |
| 2007/0038141 A1 | 2/2007 | Koch | |
| 2008/0195348 A1 | 8/2008 | Shidemantle et al. | |
| 2008/0300819 A1 | 12/2008 | Koch | |
| 2009/0299682 A1 | 12/2009 | Yarden et al. | |

OTHER PUBLICATIONS

U.S Appl. No. 12/130,238 Official Action dated Dec. 27, 2010.

* cited by examiner

*Primary Examiner* — Gail Verbitsky
(74) *Attorney, Agent, or Firm* — D. Kligler I.P. Services Ltd.

(57) ABSTRACT

Thermometric apparatus includes at least one body-surface sensor, which is configured to be placed at a location on a body surface of a patient and generates a sensor output that varies according to a body-surface temperature at the location. Analog conversion circuitry is coupled between the at least one body-surface sensor and a connector for coupling to a patient monitor. The circuitry is configured to convert the sensor output into an output resistance across the connector that is indicative of a corrected temperature of the patient.

20 Claims, 6 Drawing Sheets

TEMPERATURE SENSOR WITH CALIBRATED ANALOG RESISTIVE OUTPUT

FIELD OF THE INVENTION

The present invention relates generally to temperature measurement and monitoring, and specifically to methods and systems for non-invasive body temperature measurement.

BACKGROUND OF THE INVENTION

Continuous, accurate measurement of core-body temperature is an important tool in monitoring the well-being of a patient. Traditionally, core-body temperature has been measured using invasive devices, such as probes in the esophagus placed close to the heart or probes in the bladder inserted via the urinary tract. Such probes are generally unsuitable for monitoring patients not under anesthesia. Therefore, various non-invasive sensing devices have been developed, which estimate and output the core-body temperature based on body-surface measurements. Devices of this sort are described, for example, in U.S. Pat. No. 7,625,117 and in U.S. Patent Application Publication 2009/0299682, whose disclosures are incorporated herein by reference.

Many vital signs monitors include a standard plug for connecting to a thermistor-based temperature probe. Probes of this type were originally developed and standardized by YSI Inc. and include the YSI 400 and YSI 700 types. Such probes include a thermistor sensor, with a calibrated temperature response, and a cable with a standard connector for plugging into the monitor. The vital signs monitor simply measures the resistance value across the output connector of the cable. The monitor calculates and displays the temperature according to the measured resistance and the known calibration curve.

U.S. Pat. No. 7,641,390, whose disclosure is incorporated herein by reference, describes a method for digitally controlling the resistive output of a temperature probe. The method uses a temperature sensor, a processor and a means under the control of the processor for modifying the resistive output, such as a digital potentiometer. In one embodiment, the processor reads the temperature sensor and adjusts the potentiometer based on a correlative or predictive technique so as to provide a modified output that matches that of a standard resistive temperature probe and is compatible for display on a multi-parameter monitor.

SUMMARY OF THE INVENTION

Embodiments of the present invention that are described hereinbelow provide temperature sensing devices and methods capable of providing a resistive output that is indicative of a corrected temperature, such as a core-body temperature, using a body-surface temperature sensor and analog resistance conversion circuits.

There is therefore provided, in accordance with an embodiment of the present invention, thermometric apparatus, including at least one body-surface sensor, which is configured to be placed at a location on a body surface of a patient and generates a sensor output that varies according to a body-surface temperature at the location. A connector is coupled to a patient monitor. Analog conversion circuitry is coupled between the at least one body-surface sensor and the connector and is configured to convert the sensor output into an output resistance across the connector that is indicative of a corrected temperature of the patient.

Typically, the output resistance is proportional to a core-body temperature of the patient in accordance with a calibration function of a standard invasive temperature probe.

In disclosed embodiments, the at least one body-surface sensor includes at least one thermistor. In some embodiments, the at least one thermistor includes a plurality of thermistors, which are connected to the analog resistance-conversion circuitry in a circuit topology selected so as to implement a conversion function between the thermistor resistance value of the body-surface thermistors and the output resistance. In one embodiment, the at least one body-surface sensor includes a substrate on which the thermistors are arranged in a physical interleaving such that the thermistors from different parts of the circuit topology are physically mutually adjacent.

In some embodiments, the apparatus includes at least one ambient-measurement sensor, which is configured to sense an ambient temperature in a vicinity of the patient and is coupled to the analog resistance-conversion circuitry along with the at least one body-surface sensor in a circuit topology selected so as to implement a conversion function that generates the output resistance. In one embodiment, the at least one body-surface sensor and the at least one ambient-measurement sensor together include at least one negative temperature coefficient (NTC) thermistor and at least one positive temperature coefficient (PTC) thermistor. Additionally or alternatively, the apparatus includes a cable coupled between the at least one body-surface sensor and the connector, wherein the at least one ambient-measurement sensor is mounted on the cable.

In some embodiments, the at least one ambient-measurement sensor includes an active circuit for generating a specified functional dependence of the output resistance on the ambient temperature. The active circuit may be a digital circuit.

Alternatively, the apparatus includes only passive circuit components. In one embodiment, the analog resistance-conversion circuitry includes a network of resistors coupled to the at least one sensor.

In another embodiment, the analog resistance-conversion circuitry includes a photoresistor and an optoemitter, which is coupled to drive the photoresistor in response to a thermistor resistance value.

In a disclosed embodiment, the apparatus includes a skin patch, which contains the at least one sensor and at least a part of the analog resistance-conversion circuitry and is configured to be affixed to the body surface of the patient.

In another embodiment, the apparatus includes a wireless transmitter, which is coupled to the body-surface sensor so as to generate and transmit over the air a signal indicative of the sensor output, and a wireless receiver, which is coupled to the connector so as to receive the signal and to cause the output resistance to be generated across the connector responsively to the signal.

There is also provided, in accordance with an embodiment of the present invention, a method for thermometry, including placing at a location on a body surface of a patient at least one body-surface sensor, which generates a sensor output that varies according to a body-surface temperature at the location. Analog resistance-conversion circuitry is coupled to the at least one body-surface thermistor so as to convert the thermistor resistance value into an output resistance that is indicative of a corrected temperature of the patient. The output resistance is coupled to an input of a patient monitor.

The present invention will be more fully understood from the following detailed description of the embodiments thereof, taken together with the drawings in which:

DETAILED DESCRIPTION OF EMBODIMENTS

As noted in the Background, many existing patient monitoring systems are factory-configured to receive a resistive temperature reading. These systems were designed and calibrated to operate with standard invasive thermistor probes, such as a YSI 400 or YSI 700-type probe, and to convert the output resistance of the probe directly into a core temperature reading. A body-surface thermistor probe could also be plugged into the monitoring system, but the temperature reading that it gives will not accurately reflect the core body temperature. Deriving the core-body temperature from the measured body-surface temperature typically requires application of a conversion function, which may include the ambient temperature, as well as multiplicative and/or additive factors.

Embodiments of the present invention that are described hereinbelow apply this sort of conversion function using analog resistance-conversion circuitry. This circuitry is coupled to at least one body-surface sensor, such as a thermistor, and possibly to an ambient-measurement sensor, as well, in a certain circuit topology together with other analog components. The topology and components are chosen so that the output resistance of the circuitry is indicative of a corrected temperature, typically the core-body temperature of the patient. In other words, the circuitry is arranged to give, on the basis of a body-surface thermistor, approximately the same output resistance as would an invasive thermistor probe in the patient's body. The resistance conversion is performed directly, without any need to convert the measured resistance values into digital form and then re-convert the digital values back to resistance.

The analog resistance-conversion circuitry is coupled to a cable with a standard connector for plugging into a patient monitor. The patient monitoring system will then properly display the core body temperature, based on the output resistance across the connector, without requiring any additional calibration or modification to the system, despite the resistance reading having been provided by a body-surface thermistor. The disclosed embodiments thus provide simple, inexpensive means for deriving core-body temperature readings from body-surface sensors, which are fully backward-compatible with existing monitoring systems.

Figure 1:
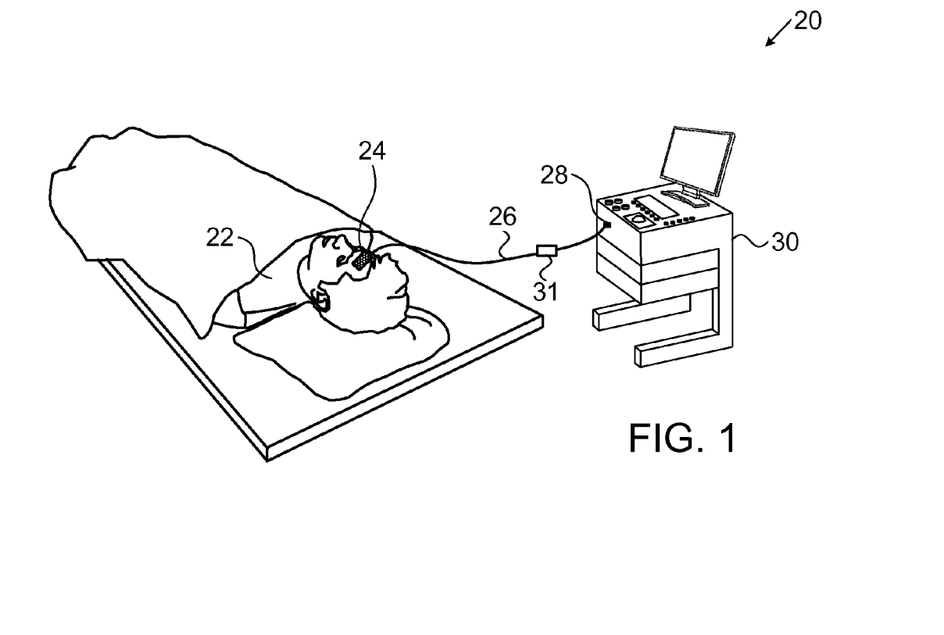
FIG. 1 is a schematic, pictorial illustration of a system for patient monitoring, in accordance with an embodiment of the present invention.

FIG. 1 is a schematic, pictorial illustration of a patient monitoring system 20, in accordance with an embodiment of the present invention. The system typically monitors multiple physiological parameters of a patient 22 in an operating room or hospital ward, but only the parts of the system that are involved in temperature measurement are shown here. A temperature-sensing patch 24 is affixed to the patient's body surface, such as to the skin of the patient's forehead or elsewhere on the body. Patch 24 comprises one or more thermistors, which measure the body-surface temperature, along with analog resistance-conversion circuitry and possibly one or more ambient-measurement thermistors. (These elements are not shown in FIG. 1 but are described in detail below.) Alternatively, an ambient sensing probe 31 may optionally be mounted on a cable 26 connected to patch 24.

Patch 24 is connected via cable 26 to a connector 28, which terminates the cable and plugs into a patient monitor 30. The patient monitor typically comprises a computer processor, with suitable input circuits for receiving signals from various physiological sensors. The input circuits include a standard receptacle for receiving plug 28. Monitor 30 measures the resistance across plug 28 and converts the resistance to a core temperature value according to a pre-programmed calibration function. The monitor typically displays the resulting temperature measurement and may also track the value over time and issue alarms when the temperature moves outside a preset safety range.

Figure 2A:
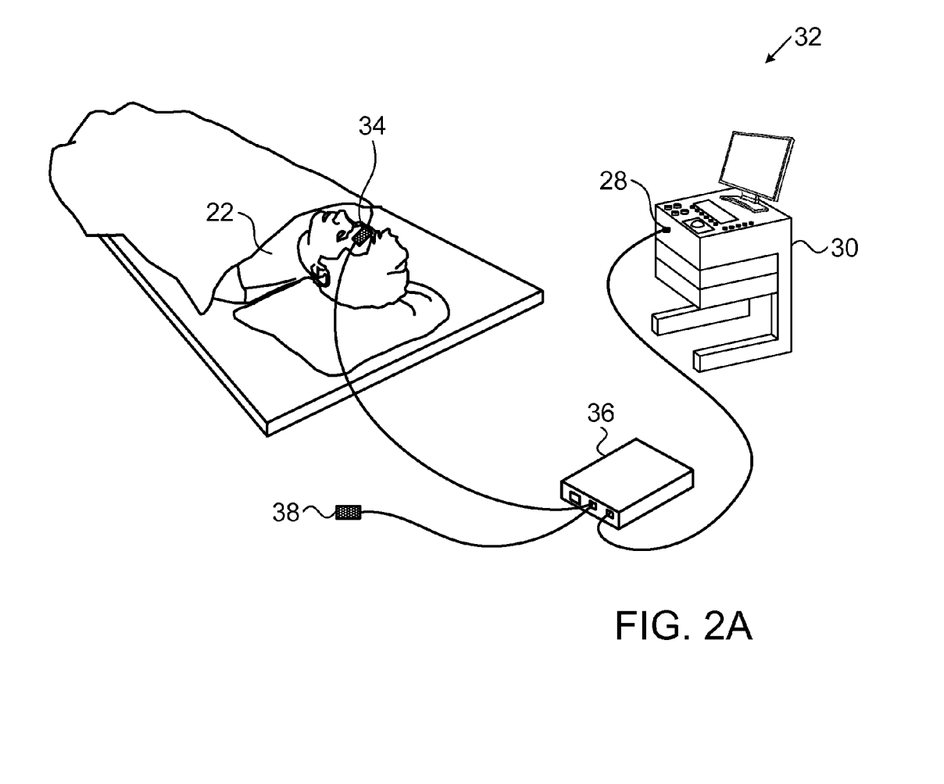
FIGS. 2A and 2B are schematic, pictorial illustrations of systems for patient monitoring, in accordance with other embodiments of the present invention.

FIG. 2A is a schematic, pictorial illustration of a patient monitoring system 32, in accordance with an embodiment of the present invention. The principles of operation of system 32 are similar to those of system 20, as described above, but in system 32 a temperature-sensing patch 34 on the patient's body measures only the body-surface temperature (or temperatures) and possible other vital signs. Analog resistance-conversion circuitry 36 is contained in a separate enclosure and is connected by a cable to patch 34. An ambient sensing probe 38 contains one or more ambient-measurement thermistors. Patch 34 and probe 38 are connected via cables to circuitry 36. Alternatively, ambient sensing probe 38 may be mounted on the enclosure of circuitry 36.

Figure 2B:
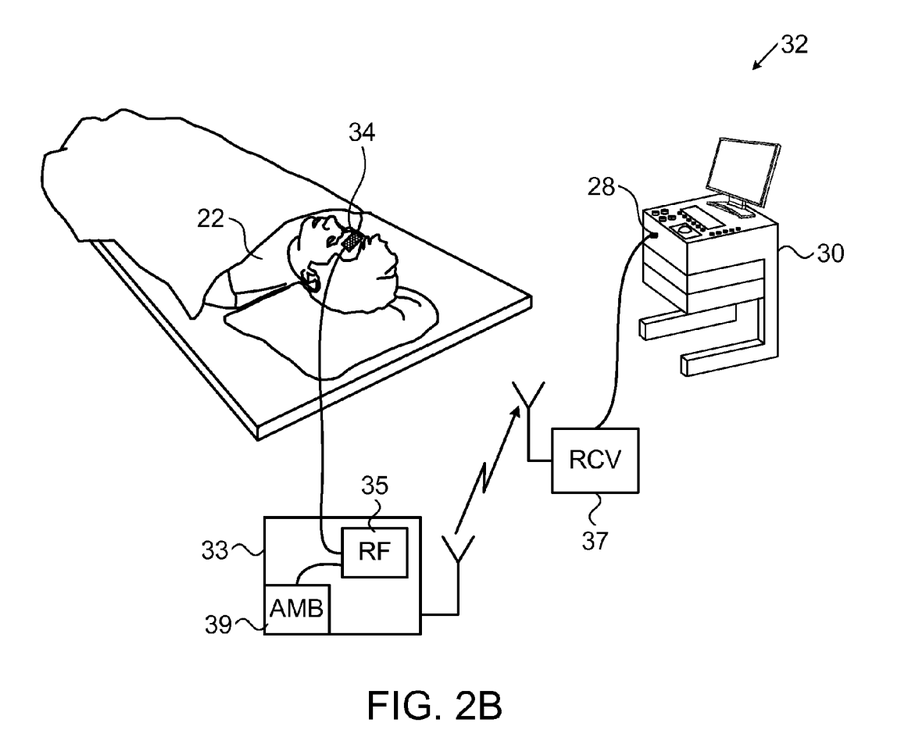

FIG. 2B is a schematic, pictorial illustration of system 32 in an alternative configuration, in accordance with another embodiment of the present invention. In this embodiment, a bedside unit 33 receives signals from patch 34 and from an ambient sensing probe 39. A radio frequency (RF) transmitter 35 in or connected to unit 33 generates a wireless signal to a receiver 37. (Alternatively, bedside unit 33 may transmit other sorts of wireless signals, such as an infrared signal. Further alternatively or additionally, some or all of the elements of unit 33 may be integrated in patch 34.) Transmitter 35 modulates the signal to indicate the resistance values output by patch 34 and probe 39. Receiver 37 demodulates the signal and generates the appropriate analog output resistance across connector 28.

In other embodiments, not shown in the figures, alternative system configurations may be used. For example, analog resistance-conversion circuitry 36 may be integrated with patch 34. Alternatively, one or more ambient-measurement thermistors may be integrated with patch 34, thus obviating probe 38, while circuitry 36 is housed in a separate unit.

As another alternative, ambient probe 38 or 39 may comprise digital processing circuitry (while patch 34 remains fully analog). This configuration provides added flexibility in generating the ambient correction component in the appropriate proportion and polarity relative to the body-surface measurement, while maintaining the simplicity and reliability of the all-analog body-surface patch.

Figure 3:
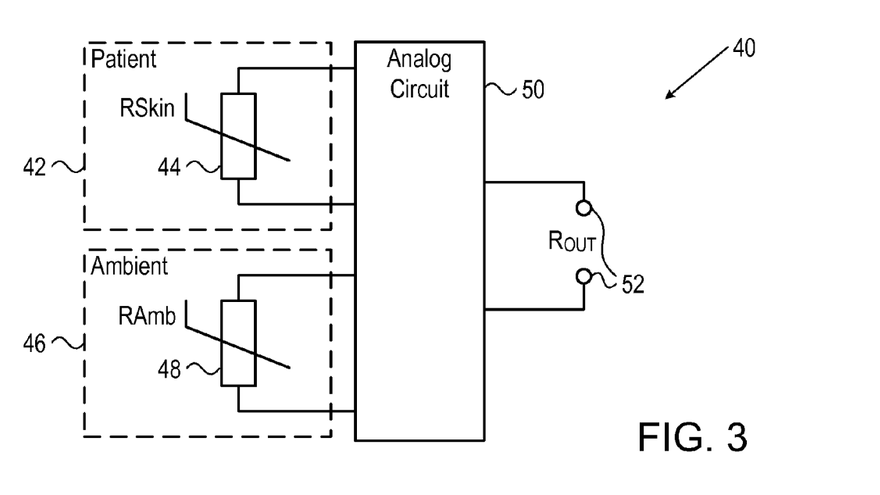
FIGS. 3-6 are schematic circuit diagrams of temperature measurement devices, in accordance with embodiments of the present invention.

FIG. 3 is a schematic circuit diagram of a temperature monitoring device 40, in accordance with an embodiment of the present invention. FIG. 3 presents a conceptual picture of the elements of such a device, while the figures that follow show more specific designs. Device 40 comprises a body-surface probe 42 (such as a skin patch) and an ambient sensing probe 46, which may be integrated with the body surface probe or the cable or contained in a separate unit, as illustrated in FIGS. 1, 2A and 2B. Probe 42 contains at least one body-surface thermistor 44, which has a variable resistance value $R_{skin}$ that is indicative of the body-surface temperature. Probe 46 similarly contains at least one ambient-measurement thermistor 48, which has a variable resistance value $R_{amb}$, which is indicative of the ambient temperature.

Alternatively, because the ambient resistance value $R_{amb}$ typically makes only a small contribution (relative to $R_{skin}$) to the core-body temperature output of device 40, thermistor 48 may, in some embodiments, be replaced by a fixed resistor of appropriate value. Alternatively, thermistor 48 may be replaced by a set of two or more selectable resistors with a switch, which a user of the device can set depending on the ambient temperature range. Further alternatively, the switch may be set automatically, using a thermostat, for example.

Thermistors 44 and 48 are connected to analog resistance-conversion circuitry 50, which has a circuit topology and components that are arranged to generate an output resistance $R_{out}$ across terminals 52, which connect to plug 28. The output resistance is typically a linear combination of the form $R_{out} = A*R_{skin} + B*R_{amb} + R_c$, wherein A and B are multiplicative coefficients and $R_c$ is an additive constant bias resistance. The values of A, B and $R_c$ are typically chosen based on the correspondence between the core-body temperature and the skin and ambient temperatures, so that $R_{out}$ is approximately equal to the output resistance that would be generated by a standard invasive thermistor probe (such as a YSI 400 or YSI 700-type probe) under these conditions. Typically, body-surface thermistor 44 is a negative temperature coefficient (NTC) thermistor, but ambient-measurement thermistor 48 may be a positive temperature coefficient (PTC) thermistor if the coefficient B in the above equation is negative. (Alternatively, a NTC thermistor may be used with a digital circuit to generate an ambient temperature correction of the desired sign.)

Figure 8A:
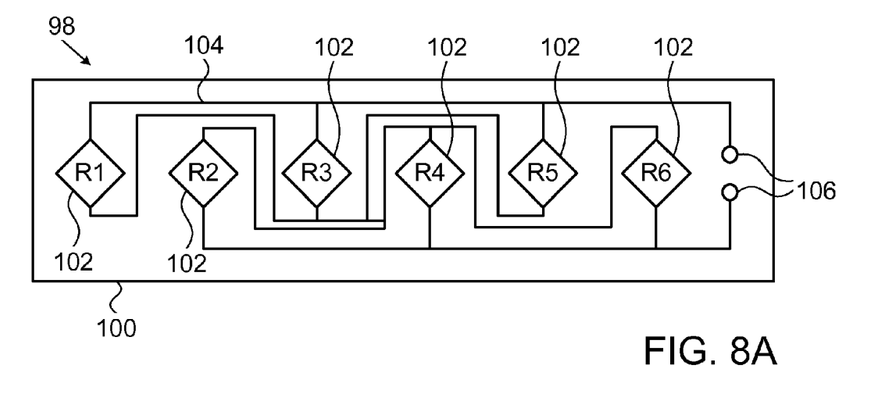
FIG. 8A is a schematic frontal view of a temperature sensing patch, in accordance with an embodiment of the present invention.
Figure 8B:
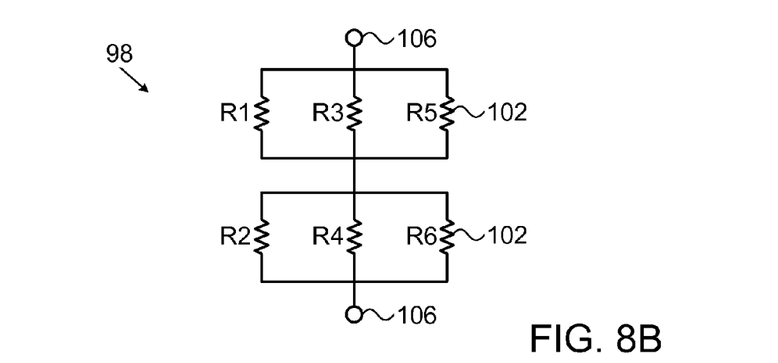
FIG. 8B is a schematic circuit diagram of the patch of FIG. 8A.

Although only a single body-surface thermistor and a single ambient-measurement thermistor are shown in FIG. 3, device 40 may alternatively comprise multiple body-surface and/or ambient-measurement thermistors, in series or in parallel, in order to implement multiplication by A and B. The use of an array of thermistors is also helpful in averaging out local temperature variations over the skin surface. (FIGS. 8A and 8B show an embodiment that takes advantage of this feature.)

Temperature sensing devices in accordance with the principles outlined above may comprise only analog passive circuit components (including the thermistors), such as a network of resistors. Optionally, active analog components may also be used. As another option, the temperature sensing device may comprise a digitally-controlled circuit, which converts an analog sensor value (such as a resistance or voltage) into a digital value, which is then processed and converted to a resistance value to be combined with the analog resistance output of the body-surface temperature sensor. Other characteristics of the human body can similarly be measured and converted to resistance values, which can be incorporated into the core body temperature output. These characteristics may include blood perfusion, pulse, and/or blood pressure, for example, can be processed in a similar manner to the ambient temperature values.

The following procedure may be used to calculate the resistive values used in a temperature monitoring device such as device 40:

First the appropriate functional relationship is found between the skin temperature and the core temperature T, taking into account other factors influencing this relationship, such as ambient temperature, humidity and/or physical characteristics of the patient: $T = \alpha \times T_{skin} + \beta \times T_{ambient} + \gamma \times S + Bias$, wherein S may be any physical characteristic of the human body.

Then this functional relationship is translated into a resistive circuit as illustrated by the following examples:

Say, for instance, that we can represent the core temperature using the formula:

$$T_{CORE} = \alpha \times T_S + \beta \times T_{AMB} + \gamma$$

wherein $T_S$ is the skin temperature, $T_{AMB}$ is the ambient temperature and $\alpha, \beta, \gamma$ are constants.

Using standard YSI calibration functions, temperatures can be written in terms of thermistor resistances. Over a certain limited range of temperatures, these functions can be written as linear functions of the form:

$$p^1(R_{CORE}) = \alpha \times q^1(R_S) + \beta \times r^1(R_{AMB}) + \gamma$$

Therefore we can write that:

$$R_{CORE} = A \times R_S + B \times R_{AMB} + C$$

for a limited range of temperatures and for some constants A,B,C. These constants can be determined from experimental data by minimizing the functional:

$$\epsilon = \Sigma (R_{CORE} - A \times R_S + B \times R_{AMB} + C)^2$$

The minimization is accomplished when $$\frac{d\epsilon}{dA} = \frac{d\epsilon}{dB} = \frac{d\epsilon}{dC} = 0.$$

The circuit described by the previous equations should desirably represent the best possible approximation of the function produced in the previous step. More complicated functions, such as higher-order polynomials, can be represented using active analog circuits, if the function that relates the core temperature to the measured parameters is more complex than a linear function.

After the design of the circuit is finalized, the particular values of the components may be adjusted to satisfy the requirements of the output, such as compliance with the YSI 400 standard core-body temperature/resistance relations. $R = \alpha \times T^3 + \beta \times T^2 + \gamma \times T + \delta$ For example, the component values may be optimized by fitting the output resistance to the standard core-body temperature/resistance relations using the least-squares method or variational techniques. Parameters other than temperatures, such as the local blood flow and the fat content of the patient, are also known to have a role in the relation between body-surface and core-body temperatures. These parameters can also be represented using selectable resistive values in analog resistance-conversion circuitry 50, and can thus be taken into consideration in generating $R_{out}$ to represent the core-body temperature with greater accuracy.

Additionally or alternatively, device 40 may be adjustable to simulate different types of outputs, such as emulating the response of an esophageal temperature probe or a urinary temperature probe. The adjustment may be made, for example, by flipping a hardware switch between resistor configurations corresponding to different emulation models.

Figure 4:
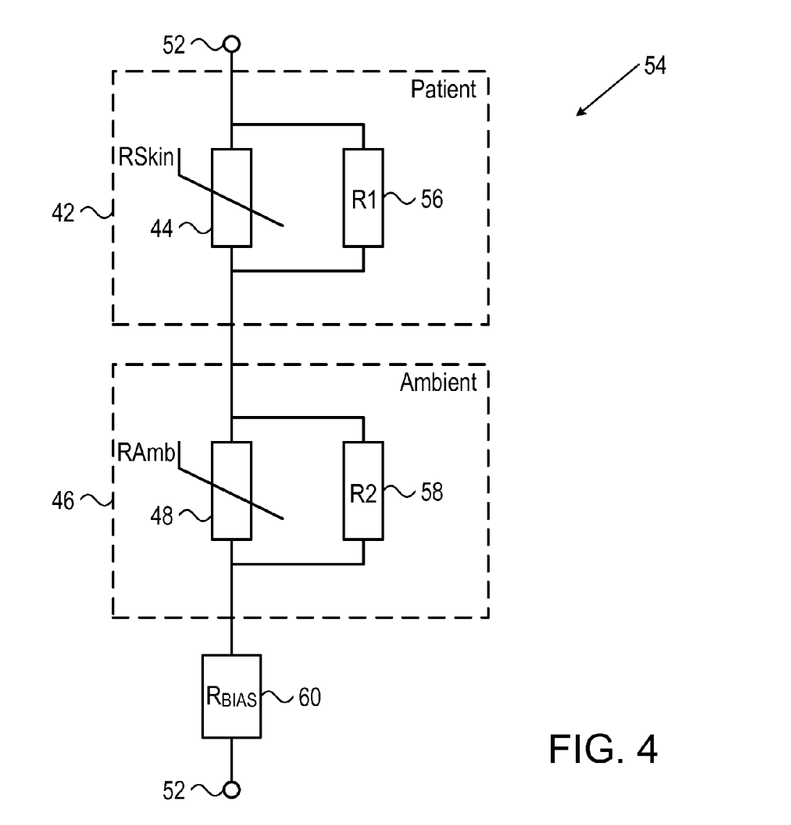
Figure 5:
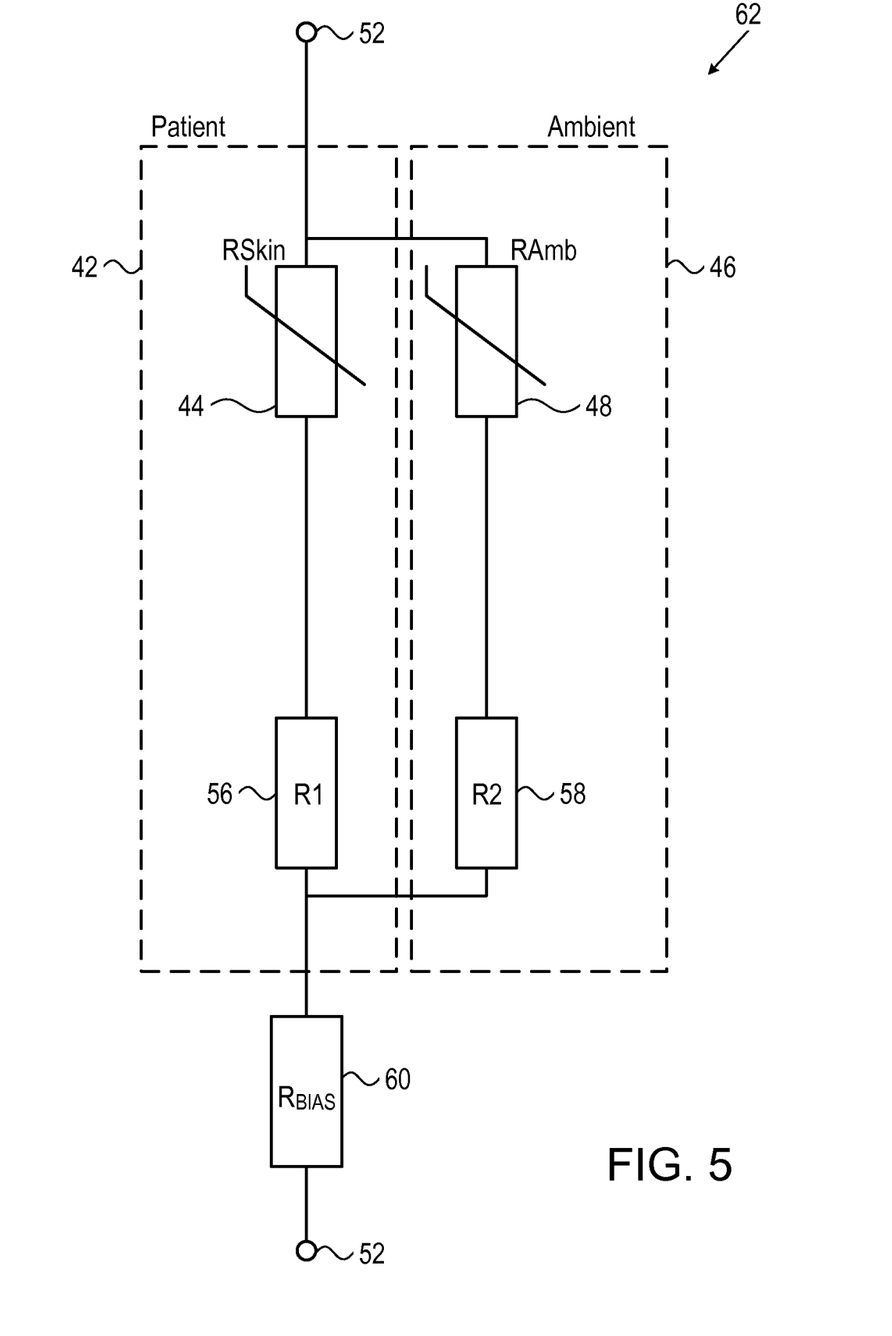

FIGS. 4 and 5 are schematic circuit diagrams of temperature measurement devices 54 and 62, respectively, in accordance with embodiments of the present invention. Device 54 illustrates a series circuit configuration, in which the resistance values of body-surface probe 42 and ambient sensing probe 46 are added together along with a constant series resistance 60, $R_{bias}$. In this particular configuration, parallel resistances 56 and 58, with values R1 and R2, moderate the resistance values of body-surface and ambient-measurement thermistors 44 and 48. By contrast, in device 62, body-surface probe 42 and ambient sensing probe 46 are arranged in parallel, while respective resistances 56 and 58 are in series with thermistors 44 and 48.

The particular topologies of FIGS. 4 and 5 are shown solely by way of example, and other, more complex topologies, which may combine parallel and serial features, may also be used. Furthermore, as shown in the examples that follow, it may be advantageous to use multiple thermistors in a parallel and/or serial network, instead of or in addition to resistors 56 and 58.

Figure 6:
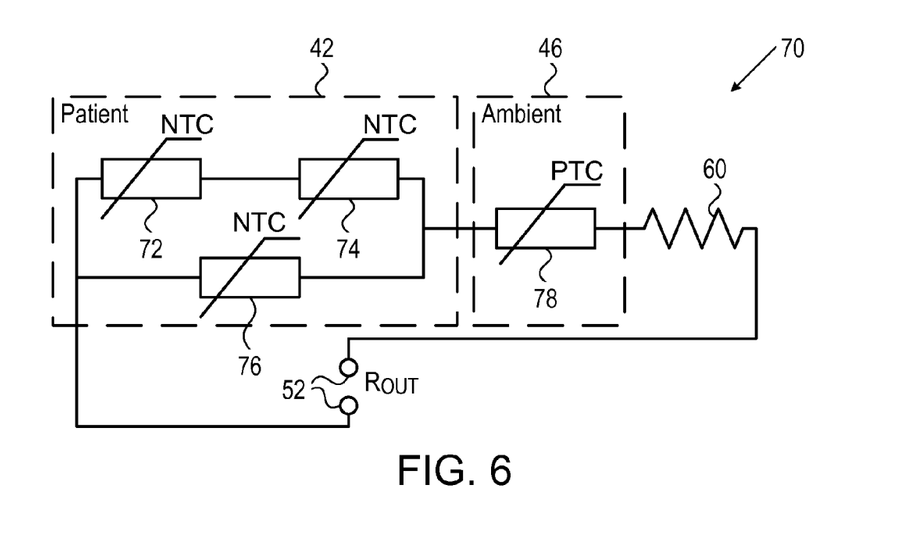

FIG. 6 is a schematic circuit diagram of a temperature measurement device 70, in accordance with another embodiment of the present invention. In this embodiment, body-surface probe 42 comprises multiple, identical thermistors 72, 74 and 76 in a series/parallel network. Ambient sensing probe 46 in this embodiment (and, typically, in the preceding embodiments, as well) comprises a single PTC thermistor 78, but in alternative embodiments, the ambient sensing probe may likewise comprises multiple thermistors. The thermistors in both of probes 42 and 46 may be arranged in parallel, in series, or in a combined series/parallel topology, such as that shown in FIG. 6.

Device 70 implements the typical conversion formula:

$$T = 0.66 \times T_{skin} - 0.17 \times T_{ambient} + \text{Bias}$$

Assuming thermistors 72, 74 and 76 to be of the same standard NTC type as is used for core body measurement, each with temperature-dependent resistance $R_{skin}$, the above equation can be restated in terms of the resistances:

$$R_{out} = 0.66 \times R_{skin} - R_{ambient} + R_{bias}$$

This formula assumes that PTC thermistor 78 conveniently has a temperature-dependent resistance $R_{ambient}$ with a positive slope that is 0.17 times the negative slope of the NTC thermistors. Alternatively, multiple thermistors and/or resistors may be arranged in series and/or parallel in place of the single thermistor 78 in order to achieve the desired proportionality. The resistance of the parallel/serial network of thermistors 72, 74, 76 is 0.66 times the resistance of a single one of the thermistors. Other topologies can be used to realize other coefficient values for both $R_{skin}$ and $R_{ambient}$. $R_{bias}$ is provided by the value of resistor 60.

For example, assume that at an ambient temperature of 25° C. and a core-body temperature of 37° C., the temperature of the skin is 33° C. At 33° C. the resistance of standard NTC thermistors 72, 74 and 76 is 1600Ω, so that the resistance of probe 42 is 1067Ω. According to the YSI 400 standard, the value of resistance equivalent to 37° C. is 1357Ω. Therefore, the combination of $R_{ambient}$ at 25° C. with $R_{bias}$ should be about 300Ω. After choosing PTC thermistor 78, the bias resistance is chosen to give the desired sum.

Figure 7:
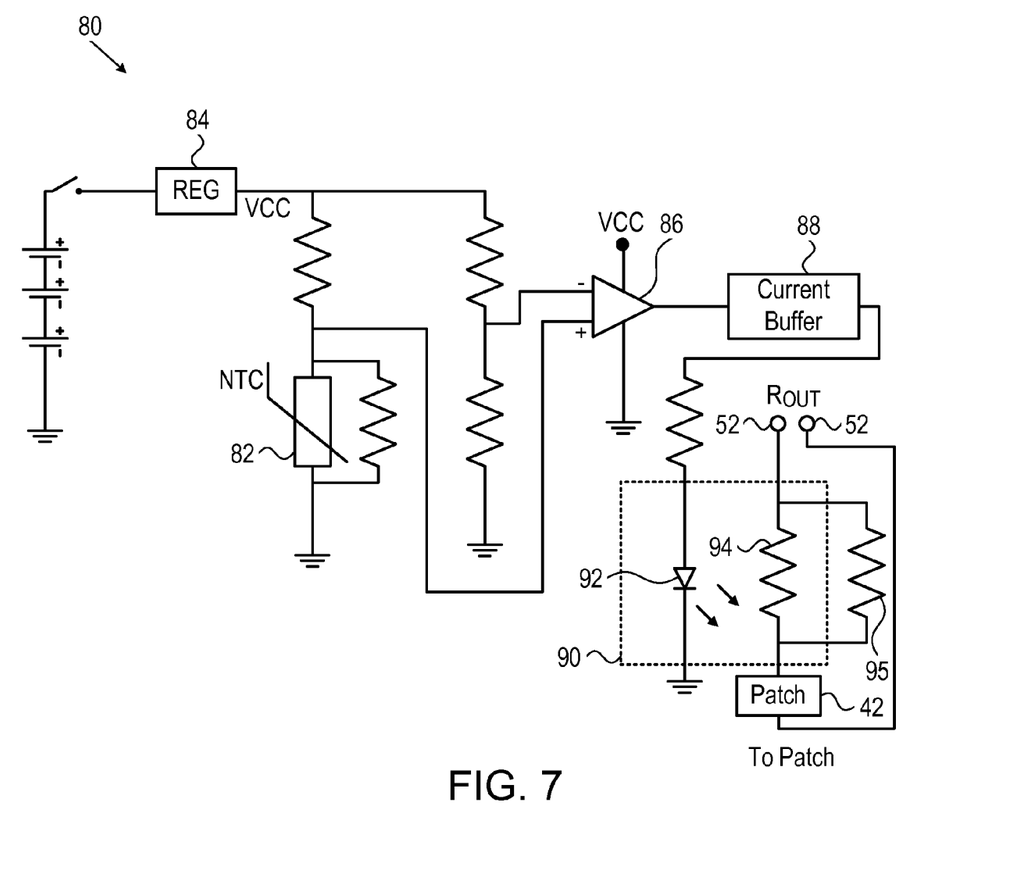
FIG. 7 is a schematic circuit diagram of an ambient sensing probe, in accordance with an embodiment of the present invention.

FIG. 7 is a schematic circuit diagram of an ambient temperature sensing probe 80, in accordance with an embodiment of the present invention. This circuit may be used in place of probe 46 in device 70 (FIG. 6), for example, in order to give more precise control over the $R_{ambient}$ term in the total output resistance of the device. In probe 80, a voltage regulator 84 provides a Vcc voltage level, such as 3.3 volts, to a pair of resistive voltage dividers, one of which is controlled by a NTC thermistor 82. The voltage difference between the central nodes of the two voltage dividers is amplified by a differential amplifier 86 and drives an optocoupler 90 through a current buffer 88. The optocoupler comprises an optoemitter 92, such as a light-emitting diode (LED), which irradiates a photoresistor 94 with a flux level dictated by the driving current. The photoresistor is coupled in series between body-surface probe 42 and connector 28 to monitor 30 (FIGS. 1 and 2). A parallel resistor 95 may be added for adjustment.

Thus, probe 80 provides a resistance on photoresistor 94 that varies with the ambient temperature, with a slope that can be adjusted by appropriate choice of resistors and amplifier gain. This probe circuit can be arranged to emulate either a positive or a negative temperature coefficient. Although this probe is more complex that the all-passive circuit designs described above, it still uses only inexpensive analog components.

FIGS. 8A and 8B schematically illustrate a temperature sensing patch 98, in accordance with another embodiment of the present invention. FIG. 8A is a frontal view of the patch, while FIG. 8B shows the electrical circuit embodied in the patch. Patch 98 comprises six thermistors 102 (labeled R1, . . . , R6), which are mounted on a flexible printed circuit substrate 100. The thermistors are interconnected by conductors 104 on the substrate, defining the circuit shown in FIG. 8B. Assuming the thermistors all to have equal resistance R, an output resistance equal to ⅔ R will be measured at terminals 106 of the patch. (If the resistances are not exactly equal, the deviation in the output resistance will still be only second-order in the error. The thermistors may be sorted and selected during production to minimize the differences between them.) Patch 98 is typically used in conjunction with a suitable ambient sensing probe, as described above; but in an alternative embodiment, without ambient corrections, terminals 106 may be connected directly to plug 28.

The physical locations of thermistors 102 on substrate 100 do not directly reflect their topological locations in the circuit. Rather, thermistors from different parts of the circuit are interleaved, so that thermistors from different parts of the circuit topology are physically mutually adjacent. This interleaving is useful in providing accurate body-surface temperature measurements, notwithstanding local variations in the skin temperature, which commonly occur. Thus, if the patient's skin under the left side of patch 98 in FIG. 8A is warmer than the right side, for example, the higher temperature will be felt mainly in thermistors R1 and R2, and the effect will be spread roughly equally over the upper and lower sub-networks in FIG. 8B.

Figure 9:
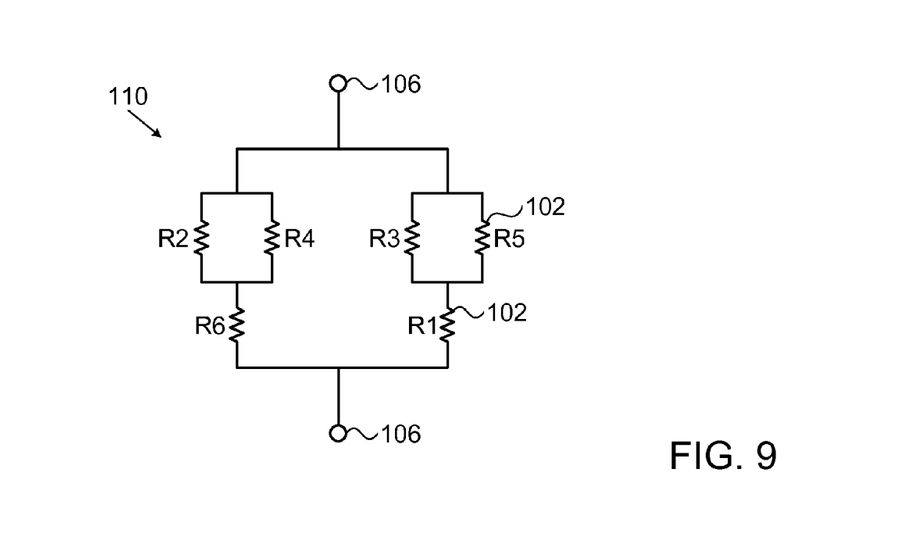
FIG. 9 is a schematic circuit diagram of a temperature sensing patch, in accordance with another embodiment of the present invention.

FIG. 9 is a schematic circuit diagram of a temperature sensing patch 110, in accordance with another embodiment of the present invention. In this case, the output resistance across terminals 106 will be ¾ R. The physical locations of the thermistors in the patch may be as shown in FIG. 8A (with a different layout of conductors 104), or may use another interleaving.

Although the embodiments described above relate specifically to conversion of skin temperature measurements into core-body temperature values, the principles of the present invention may similarly be used in other applications of on-line temperature measurement, as well as for measurement and monitoring of other physical characteristics of the human body. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Thermometric apparatus, comprising:
   at least one body-surface sensor, which is configured to be placed at a location on a body surface of a patient and generates a sensor output that varies according to a body-surface temperature at the location;
   a connector for coupling to a patient monitor; and
   analog conversion circuitry, which is coupled between the at least one body-surface sensor and the connector and consists only passive components, which are configured to convert the sensor output by means of an analog operation into an output resistance across the connector that is indicative of a corrected temperature of the patient, without conversion of the sensor output into digital form and re-conversion of digital values back to resistance.

2. The apparatus according to claim 1, wherein the output resistance is proportional to a core-body temperature of the patient in accordance with a calibration function of a standard invasive temperature probe.

3. The apparatus according to claim 1, wherein the at least one body-surface sensor comprises at least one thermistor.

4. The apparatus according to claim 3, wherein the at least one thermistor comprises a plurality of thermistors, which are connected to the analog resistance-conversion circuitry in a circuit topology selected so as to implement a conversion function between the thermistor resistance value of the body-surface thermistors and the output resistance.

5. The apparatus according to claim 4, wherein the at least one body-surface sensor comprises a substrate on which the thermistors are arranged in a physical interleaving such that the thermistors from different parts of the circuit topology are physically mutually adjacent.

6. The apparatus according to claim 1, and comprising at least one ambient-measurement sensor, which is configured to sense an ambient temperature in a vicinity of the patient and is coupled to the analog resistance-conversion circuitry along with the at least one body-surface sensor in a circuit topology implementing a conversion function that generates the output resistance.

7. The apparatus according to claim 6, wherein the at least one body-surface sensor and the at least one ambient-measurement sensor together comprise at least one negative temperature coefficient (NTC) thermistor and at least one positive temperature coefficient (PTC) thermistor.

8. The apparatus according to claim 6, and comprising a cable coupled between the at least one body-surface sensor and the connector, wherein the at least one ambient-measurement sensor is mounted on the cable.

9. The apparatus according to claim 1, wherein the analog resistance-conversion circuitry comprises a network of resistors coupled to the at least one sensor.

10. The apparatus according to claim 1, and comprising a skin patch, which contains the at least one sensor and at least a part of the analog resistance-conversion circuitry and is configured to be affixed to the body surface of the patient.

11. A method for thermometry, comprising:
    placing at a location on a body surface of a patient at least one body-surface sensor, thermistor, which generates a sensor output that varies according to a body-surface temperature at the location;
    coupling analog resistance-conversion circuitry consisting only of analog passive components to the at least one body-surface thermistor so as to convert the thermistor resistance value, using said only passive components, by means of an analog operation into an output resistance that is indicative of a corrected temperature of the patient, without conversion of the sensor output into digital form and re-conversion of digital values back to resistance; and
    coupling the output resistance to an input of a patient monitor, wherein said analog conversion circuit is coupled between the at least one body-surface thermistor and a connector coupling to the patient monitor.

12. The method according to claim 11, wherein the output resistance is proportional to a core-body temperature of the patient in accordance with a calibration function of a standard invasive temperature probe.

13. The method according to claim 11, wherein the at least one body-surface sensor comprises at least one thermistor.

14. The method according to claim 13, wherein the at least one thermistor comprises a plurality of thermistors, which are connected to the analog resistance-conversion circuitry in a circuit topology selected so as to implement a conversion function between the thermistor resistance value of the body-surface thermistors and the output resistance.

15. The method according to claim 14, wherein the at least one body-surface sensor comprises a substrate on which the thermistors are arranged in a physical interleaving such that the thermistors from different parts of the circuit topology are physically mutually adjacent.

16. The method according to claim 11, and comprising deploying at least one ambient-measurement sensor to sense an ambient temperature in a vicinity of the patient, and coupling the at least one ambient-measurement thermistor to the analog resistance-conversion circuitry along with the at least one body-surface sensor in a circuit topology selected so as to implement a conversion function that generates the output resistance.

17. The method according to claim 16, wherein the at least one body-surface sensor and the at least one ambient-measurement sensor together comprise at least one negative temperature coefficient (NTC) thermistor and at least one positive temperature coefficient (PTC) thermistor.

18. The method according to claim 16, wherein the at least one ambient-measurement sensor is mounted on the cable coupled between the at least one body-surface sensor and the input of the patient monitor.

19. The method according to claim 11, wherein the analog resistance-conversion circuitry comprises a network of resistors coupled to the at least one sensor.

20. The method according to claim 11, wherein placing the at least one body-surface sensor comprises affixing a skin patch, which contains the at least one body-surface sensor and at least a part of the analog resistance-conversion circuitry, to the body surface of the patient.

* * * * *